United States Patent [19]

Elings et al.

[11] 4,407,964

[45] Oct. 4, 1983

[54] HOMOGENEOUS FLUOROIMMUNOASSAY INVOLVING SENSING RADIATION FOR FORWARD AND BACK DIRECTIONS

[75] Inventors: Virgil B. Elings, Santa Barbara; David F. Nicoli, Goleta, both of Calif.

[73] Assignee: The Regents of The University of California, Berkeley, Calif.

[21] Appl. No.: 194,856

[22] Filed: Oct. 7, 1980

[51] Int. Cl.³ ............... G01N 33/54; G01N 33/58; G01N 33/52; G01N 21/64
[52] U.S. Cl. .................... 436/518; 250/458.1; 356/318; 356/417; 436/519; 436/520; 436/527; 436/532; 436/533; 436/534; 436/537; 436/800; 436/807
[58] Field of Search ............... 424/8, 12; 436/519, 436/520, 527, 532, 533, 534, 537, 800, 807

[56] References Cited

U.S. PATENT DOCUMENTS

| | | | |
|---|---|---|---|
| 4,193,983 | 3/1980 | Ullman | 424/8 X |
| 4,201,763 | 5/1980 | Monthony | 424/8 |
| 4,231,750 | 11/1980 | Dowben | 424/8 X |
| 4,254,096 | 3/1981 | Monthony | 424/8 |
| 4,256,834 | 3/1981 | Zuk | 424/8 |
| 4,261,968 | 4/1981 | Ullman | 424/8 |
| 4,275,149 | 6/1981 | Litman | 435/7 |
| 4,281,061 | 7/1981 | Zuk | 424/8 X |
| 4,284,412 | 8/1981 | Hansen | 424/8 X |
| 4,318,707 | 3/1982 | Litman | 23/230 B |

OTHER PUBLICATIONS

M. Weissman et al., Proc. Natl. Acad. Sci. USA, 73(8), 2776-2780 (Aug. 1976).

Rosalyn S. Yalow, Physics Today, 25-29, Oct. 1979.

Instruction Manual entitled "Immuno-Fluor, Quantitative Immunofluorescent Assay for Human Gamma Globulins", Bio-Rad Laboratories, May 1978.

Primary Examiner—Sidney Marantz
Attorney, Agent, or Firm—Poms, Smith, Lande & Rose

[57] ABSTRACT

In the course of a reaction in which one of the reactants is on the surface of carrier particles in a solution and another of the reactants is tagged with a fluorescent substance, some of the fluorescently tagged reactant attaches to, or is displaced from the carrier particle. The present invention relates to a method and device for determining the amount of fluorescently-tagged reactant which is attached to the carrier particle or which is free in solution, without physically separating the carrier particles from the solution. In a particular application of the invention (immunoassay) the reaction is between antibodies and antigens, and from the amount of fluorescently-tagged reactant which is attached to the carrier particle one can determine the unknown amount of antigen in a sample. The number of fluorescent particles which are bound to the large carrier particles and which are in solution are determined by optical and electronic sensing and analyzing techniques, including (1) shadowing techniques in which large opaque carrier particles block the pick-up of fluorescent radiation from bound tagged reactants, and/or (2) autocorrelation techniques which selectively discriminate between radiation from the bound fluorescently tagged reactants on the large particles and the free fluorescently-tagged reactants which have a more rapid diffusion movement than the carrier particles.

6 Claims, 13 Drawing Figures

HOMOGENEOUS FLUOROIMMUNOASSAY INVOLVING SENSING RADIATION FOR FORWARD AND BACK DIRECTIONS

FIELD OF THE INVENTION

The present invention relates to process analysis or immunoassay techniques.

BACKGROUND OF THE INVENTION

In connection with the diagnosis and treatment of certain health problems, it is most useful to identify and measure the various antibodies, drugs, proteins and other "macromolecules" in various body fluids. One of the most widely used techniques for making such determinations is the radioimmunoassay. The history of radioimmunoassay development is set forth, for example, in an article entitled "A Physicist In Biomedical Investigation", by Rosalind S. Yalow, *Physics Today*, October 1979, pages 25-29. The principal disadvantages of radioimmunoassays are their reliance on expensive and potentially hazardous reagents which possess a limited shelf life, the special handling and disposing procedures which are required for radioactive material, and the expensive instrumentation which is needed.

There are also several fluorescence-based immunoassay techniques which are currently in use or are undergoing clinical evaluation, with one of these techniques being described in a booklet entitled "Immuno-fluor", and subtitled "Quantitative Immunofluorescent Assay for Human Gamma Globulin", May 1978, and originating with Bio-Rad Laboratories. In one type of radiation and fluorescent immunoassay technique which has been proposed, relatively large carrier particles are coated with one of the active materials, usually the antibody, a sample to be tested is added to the solution, and the antigen in the sample is bound to the antibody. A fluorescently labeled antibody is then added to the mixture and binds to the antigen. The amount of fluorescently labeled antibody which is attached to the antigen, and is therefore bonded to the larger particles is directly proportional to the amount of the antigen in the sample. The excess fluorescently labeled antibody is then separated by standard centrifuging and decanting techniques. The remaining material consists substantially of the large particles and the attached (1) antibody, (2) antigen, and (3) fluorescently tagged antibody. The level of fluorescence of this residual material indicates the level of antigen present in the sample under test. This reaction is called a "sandwich" reaction because the antigen is sandwiched between the antibody coated to the carrier particle and the fluorescently labeled antibody.

In another immunoassay technique, carrier particles are also coated with an antibody. The coated particles, the sample with an unknown amount of antigen, and a known amount of tagged (either radioactive or fluorescent) antigen are placed in solution. The unknown antigen and the tagged antigen then complete for binding to the antibody. The carrier particles are then separated out of the solution and the amount of tagged antigen on the carrier particles is a measure of the amount of unknown antigen in the sample, the more tagged antigen bound to the carrier particles the less the unknown antigen in the sample. This type of reaction is called a competitive reaction, since the tagged antigen and unknown antigen compete for binding to the antibody which is attached to the carrier particles.

The foregoing procedures are employed in a number of radioactive-based and fluorescent-labeled assays. In each case, however, the analysis is made in the course of a reaction in which radioactive or fluorescent-tagged substances are either bound to larger particles or are shifted into solution from previous sites on the larger particles. Subsequently, the larger carrier particles are centrifuged, the residual liquid is decanted, and this is sometimes followed by additional purification steps in which liquid is added and another centifuging step is undertaken to insure the removal of any unbound component which might otherwise affect the assay signal obtained from the residue associated with the larger carrier particles.

While the prior assay techniques have proved very accurate, and are widely used, a large amount of time is spent in the separation steps; and in the case of the radioassay methods, the problem of handling the radioactive material is troublesome, and of course the undesired extra exposure to radiation is unfortunate, with its adverse health implications.

Accordingly, a principal object of the present invention is to provide an assay or analysis method which does not require the use of radioactive material, and also which does not require the physical separation of the carrier particles from the solution.

SUMMARY OF THE INVENTION

In accordance with one specific aspect of the invention, a fluorescent immunoassay technique includes the use of relatively large carrier particles with at least one active component coated on these particles, and the exposure of the particles to at least two additional active components in solution. The carrier particles may be inert particles or they may be human or animal blood cells, or other biological cells with an active component (which may be natural) on their surface. With one of the active components being fluorescently tagged, there is a shifting of some of the tagged components from solution where they are free, into a state where they are bound to the carrier particles. Subsequently, the solution (without any separation) is subjected to intense illumination which causes the fluorescently tagged materials to emit light, and optical and electronic techniques are employed to accurately determine the number of the fluorescently tagged components which have become bound to the carrier particles, or which are "free" in solution.

In accordance with one method employed to determine whether the fluorescent particles are "bound" to the larger particles or are "free", the faster diffusion rate of the "free" components as compared with those which are bound to the slower moving carrier particles, is employed to discriminate between fluorescent light originating with the two different types of particles. In one specific system, an autocorrelator is employed to suppress the signals from the faster moving "free" particles. Another technique which can contribute to the discrimination is to use carrier particles which are relatively opaque to both the incident illumination and the emitted fluorescent light. In the forward direction (direction of the incident illumination), the fluorescent light from molecules bound to the carrier particles will be "shadowed" by the opaque carrier particles compared with the light emitted in the backward direction, whereas fluorescent light from free molecules will not be shadowed in the forward direction. The difference between the fluorescent light measured at different angles with respect to the incident illumination can be used to discriminate between fluorescence arising from molecules bound to the opaque carrier particles and free molecules.

Another aspect of the invention involves the relative movement of the sample and the optical sensing path to sense a large number of different volumes within the solution, thereby improving the accuracy of the assay. Filters are also useful in discriminating against the input radiation of one optical wavelength and restricting the pickup to the fluorescent output light of a different color or wavelength.

Other objects, features and advantages will become apparent from a consideration of the following detailed description and from the accompanying drawings.

DETAILED DESCRIPTION

Figure 1:
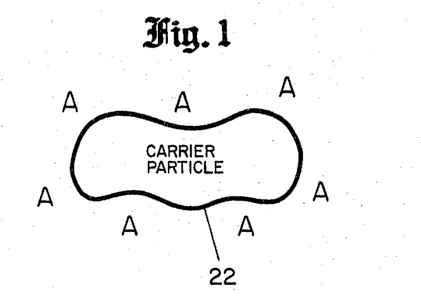
FIGS. 1, 2a and 2b are diagrammatic showings of one fluorescent immunoassay process.

The principles of the present invention will now be considered relative to an immunoassay, as illustrated in FIGS. 1. In this process, one starts with relatively large carrier particles as shown at 22 in FIG. 1 which may be made of polystyrene, latex, sephedex beads, glass spheres or some similar material. These carrier particles may also be biological cells, such as blood cells. These particles 22 as represented in FIG. 1 are coated with a given antibody, represented in FIG. 1 by the letter "A", usually by adsorption or covalent bonding. In the case of cells, the antibodies on the surface many be coated on, or may be naturally present.

Figure 2A:
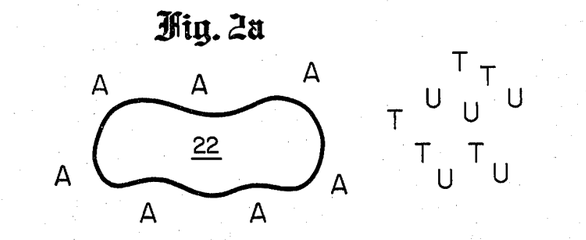
Figure 2B:
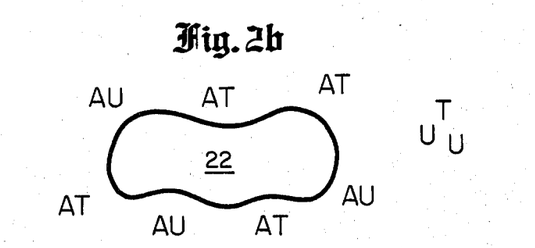

The next step as shown in FIG. 2a involves the addition of an unknown antigen sample which is to be tested along with a known amount of a fluorescently tagged antigen which is specific to the antibody A. We designate the unknown antigen by the symbol "U" and the tagged antigen by the symbol "T". Assuming that the unknown antigen is also specific to the antibody, the "U" and "T" antigens will compete for binding to the antibody as shown in FIG. 2b. The amount of T which binds to the carrier particles will depend on the amount of U in solution, since they are competing for the same binding sites. The more unknown antigen U there is in solution, the less of the known tagged antigen T that will bind to the carrier particles. The amount of T which binds to the carrier particles, or conversely, which stays free in solution, is a measure of the amount of unknown antigen U in the solution.

The solution is illuminated with a light beam whose band of wavelengths is below the band of wavelengths emitted by the fluorescent tag. For example, the fluorescent dye fluorescein emits in the yellow portion of the visible spectrum when excited by radiation in the blue-gree region of the visible spectrum. This light beam could be produced by a laser or by filtering the light from a broad-band source, such as a tungsten light, through an optical filter.

Fluorescent light which is emitted from the fluorescent tags is detected by one or more optical sensors, usually photomultiplier tubes, and filters can be placed in front of these sensors so that they are sensitive only to the fluorescent light and not the incident exciting light which is at shorter wavelengths.

Various methods have been developed for determining the amounts of free and bound fluorescently-tagged molecules which are present, without their physical separation. These methods fall into two classes: (1) discrimination between the fluorescence from tagged molecules bound to the carrier particles and the fluorescence of either tagged molecules or impurities which are "free" in solution due to the slower rate of diffusion and greater brightness of the carrier particles relative to the individual antibody and/or antigen molecules in solution, and (2) altering the angular distribution of fluorescent light emitted by the bound molecules by using opaque or semi-opaque carrier particles. These methods will be discussed in some detail below.

Figure 3:
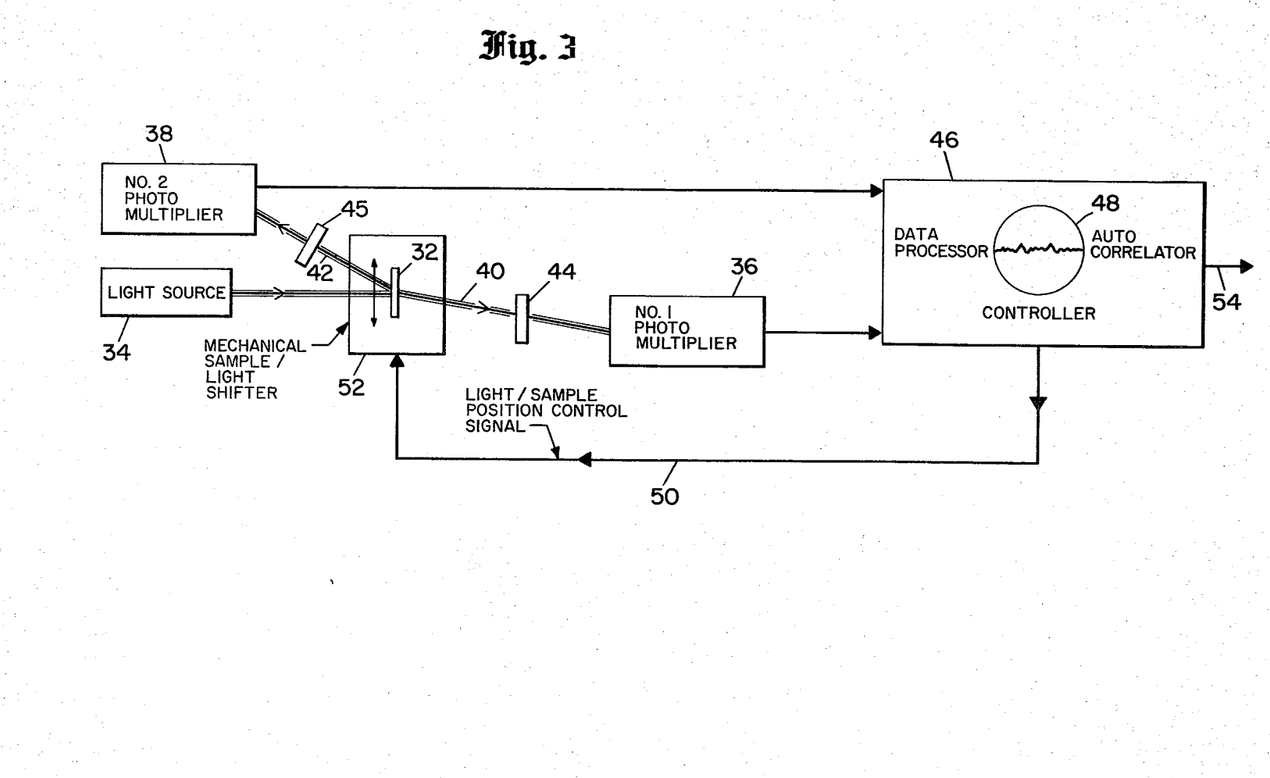
FIG. 3 is a block diagram of a typical system for the selective determination of bound and free fluorescent material in a sample.

FIG. 3 is a block diagram of the apparatus in accordance with the present invention which is employed to determine the progress of a reaction such as that shown in FIGS. 2a and 2b. More specifically, the process sample 32 to be tested is irradiated with illumination from the light source 34 with a brand of wavelengths near the peak absorbance wavelength of the fluorescent material. Light from the excited fluorescent particles or molecules will be picked up by photodetectors 36 and 38 along paths indicated at 40 and 42, respectively. Filters 44 and 45, which transmit the longer wavelength light from the excited fluorescent particles, but which block the shorter wavelength illumination from light source 34, are provided at the inputs to the photodetectors 36 and 38.

Signals from one or both of the photomultipliers 36 and 38 are transmitted to the data processing unit 46. In one particular embodiment of the invention only one photodetector is used. The data processing unit 46 may include suitable data processing circuitry for performing certain calculation functions as will be described below, including autocorrelation data processing, and will provide control signals over lead 50 to control the relative position of the optical channel and the sample 32, by arrangements indicated by block 52 in FIG. 3. This may either involve shifting the light beam relative to the sample, or physically moving the sample relative to the optical system as disclosed hereinbelow. The output from the data processing unit 46 is indicated schematically by arrow 54. This may be a digital or varying amplitude signal, or a printout, as desired. The controller 46 may be provided with two inputs, or only one, and may be operated either in a mode using the autocorrelator capability (normally with only one input) or in the shadow detection mode (normally without autocorrelation), as more fully discussed below.

Figure 4:
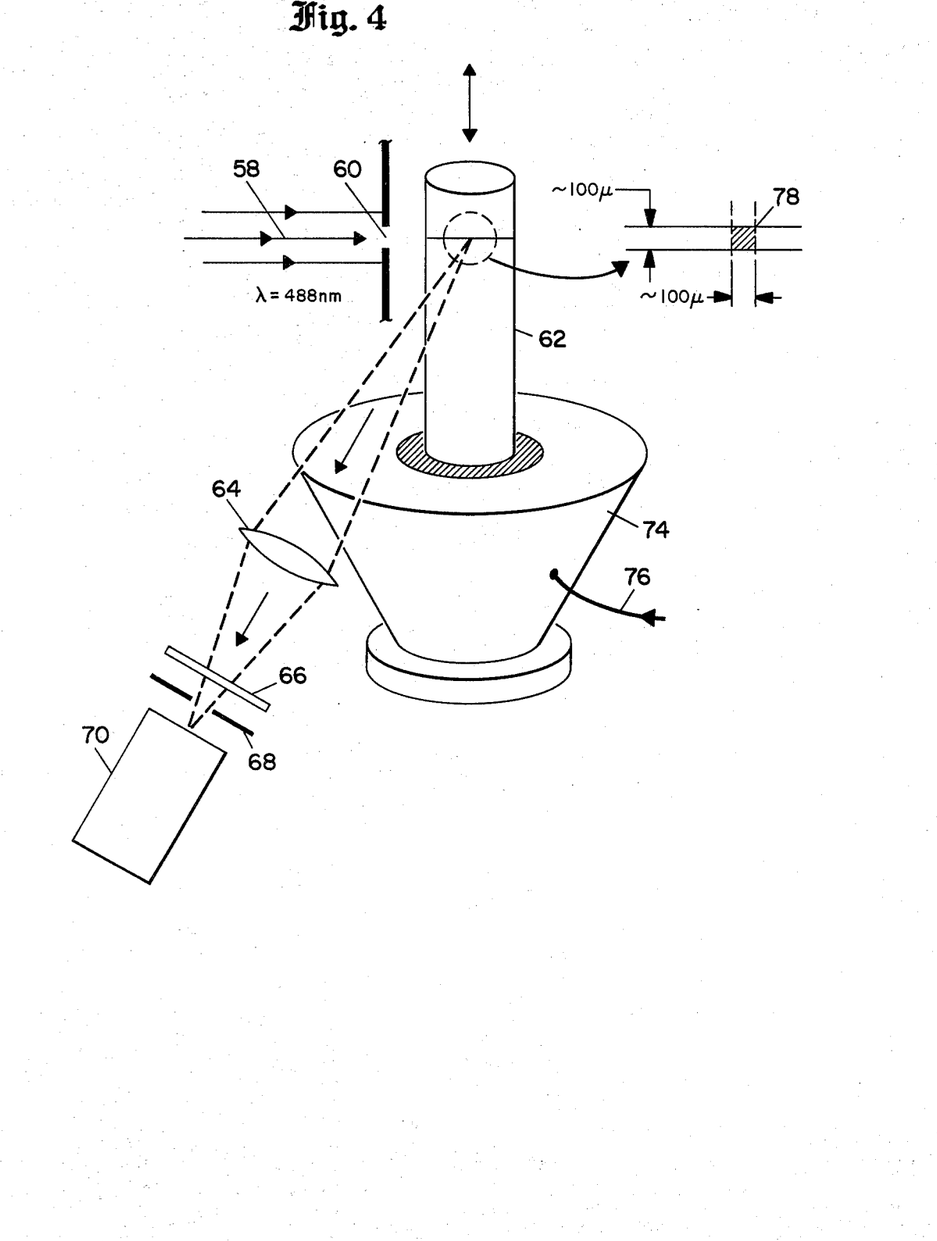
FIG. 4 is a diagrammatic showing of one apparatus which has been successfully tested.

FIG. 4 is a diagrammatic showing of one implementing apparatus which was actually employed. In FIG. 4, blue light was transmitted from an argon laser (wavelength equal to 488 mm) along a path 58 through pinhole 60 to impinge on the sample 62. The yellow-green illumination radiated by the fluorescing particles was picked up by the optical system including lens 64, filter 66, and the slit 68 to impinge on the photomultiplier tube 70. The output from photomultiplier 70 is processed by a data processor such as unit 46 of FIG. 3. The position of the sample 62 was shifted by the use of a loud speaker cone actuating arrangement 74 to which the sample 62 was attached. Input signals supplied over lead 76 from the data processing and control circuitry successively and repetitively shifted the position of the sample 62 so that different volumes were sampled. As indicated to the right in FIG. 4, the cylindrical sample volumes may be in the order of 100 microns in length and 100 microns in diameter.

Figure 5:
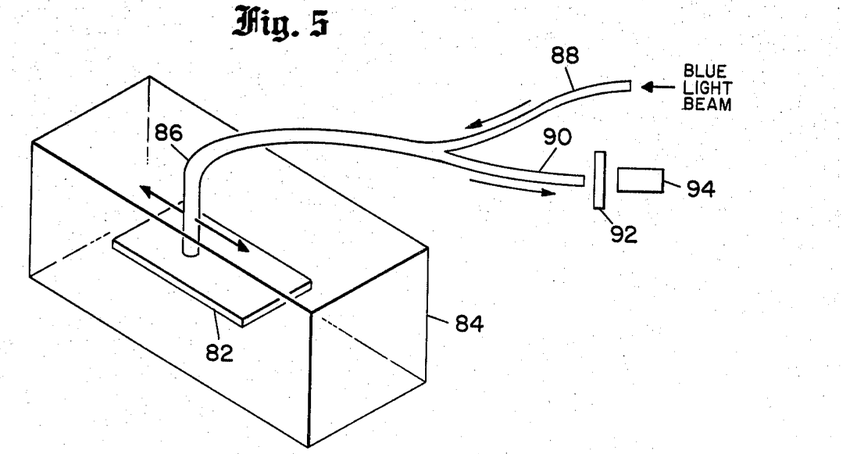
FIG. 5 is a diagrammatic showing of an alternative arrangement in which the light source and sensor probe is physically moved relative to the sample.

FIG. 5 indicates schematically one form of arrangement employing fiber optics, where the light source and pickup element are shifted relative to the sample, rather than vice versa. In FIG. 5 the thin sample cell 82 is shown mounted in a liquid container 84 to match the refractive index of the movable fiber optic element 86, thereby reducing reflections and increasing optical efficiency. The optical fiber or bundle of fibers 86 is optically coupled to two other optical fibers or bundles of fibers 88 and 90. Incident light, for example blue light, enters into the optical fiber conduit 88 and is conducted to the sample 82 by the optical fiber conduit 86. Fluorescing molecules in sample 82 provide output radiation which is picked up and transmitted over the optical fiber conduit 90. The filter 92 blocks the blue light from the original source but transmits the fluorescent radiation which might for example be yellow, through to the detector 94 which can be any suitable photo detector.

Figure 6A:
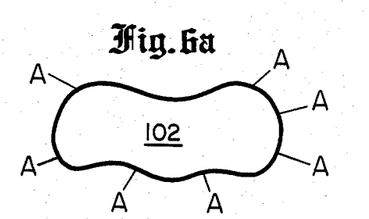
FIGS. 6a, 6b, and 6c are diagrams schematically depicting another type of immunoassay reaction.
Figures 6B, 6C:
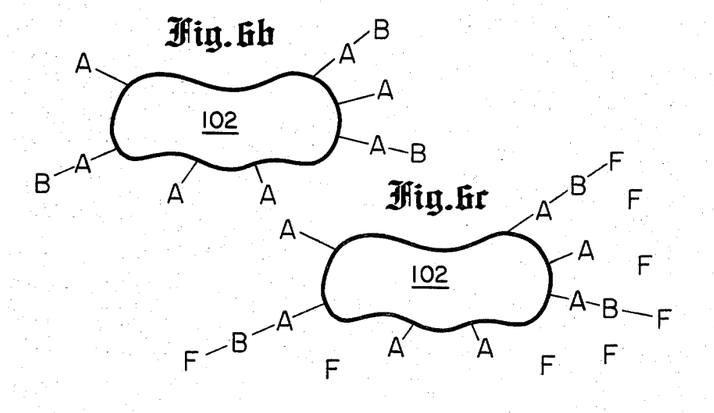

Turning now to FIG. 6, the three FIGS. 6a, 6b and 6c show successive steps in another immunoassay process. More specifically, FIG. 6a shows a large particle 102 of the type shown in FIGS. 1 and 2, with the letters "A" indicating antibodies on the beads 102 which may be plastic beads or cells, as mentioned above. The result as shown in FIG. 6a is a stable immunoadsorbent.

A sample containing an unknown amount or concentration of antigen, identified by the letter B, is added to the solution, and the resulting solution incubated at optimum temperature for a period of time. All of the antigen B is bound to the solid phase immunoadsorbent, because the immunoadsorbent is maintained in excess. This situation is shown diagrammatically in FIG. 6b.

FIG. 6c shows the situation following the addition of a fluorescently labeled antibody, which is specific to the antigen B, designated by the letter "F". Each site, as designated with the letter B symbol, has associated with it a tagged monospecific antiserum designated "F", because this antibody is added in excess. Accordingly, the fluorescent material which binds to the large particles is directly proportional to the amount of antigen supplied in the step shown in FIG. 6b; and there is also some additional free fluorescently tagged antibody F, as indicated by the letters "F" which are spaced apart from the B symbols in FIG. 6c.

Up to the point shown in FIG. 6c, the process is substantially that currently carried out commercially. In the commercial processes, the next step is to separate the unbound fluorescently tagged antibody "F" by centrifuging, and discarding the supernatant and resuspending the spun-down material in a non-fluorescing solvent, sometimes in several steps to insure purity, and then measuring the fluorescence of the residue. However, as mentioned hereinabove, these successive steps in the physical separation are time consuming and, in the aggregate, quite expensive in view of the manpower and skilled technician time which is required.

In the balance of the present specification, the techniques which have been developed by the inventors for distinguishing between bound and free fluorescently tagged material, and therefore determining the concentrations of the unknown solutions being tested, without physical separation, will be set forth. While the techniques to be described are applicable to a variety of systems, our discussion will relate primarily to the immunological applications of the type discussed broadly hereinabove. We will now proceed with a simplified mathematical analysis of the principles underlying the proposed techniques.

Let us assume that the solution contains N identical fluorescing particles per sampled volume $\delta V$. At any instant the number of particles in $\delta V$ will fluctuate according to Poisson statistics, where the root mean square (r.m.s.) magnitude of the fluctuations is equal to the square root of N. A convenient way to monitor these fluctuations is to evaluate the familiar intensity autocorrelation function, $$C(t) = <I(t') \cdot I(t'-t)>_{t'}$$

where $I(t')$ is the fluorescent intensity originating from $\delta V$ at time $t'$ and the symbol $<\ldots>_{t'}$ indicates an average of the intensity product over a large number of samples.

The usefulness of the autocorrelation function in our application depends upon the fact that a number fluctuation in $\delta V$ has a finite lifetime, where $\tau$ is the mean time for diffusion of the fluorescing particles out of (or into) the volume $\delta V$. This diffusion time is directly proportional to the hydrodynamic radius of the particle; the larger the particle, the longer the diffusion time and therefore the longer the persistence time of fluctuations in particle number in volume $\delta V$.

Figure 9:
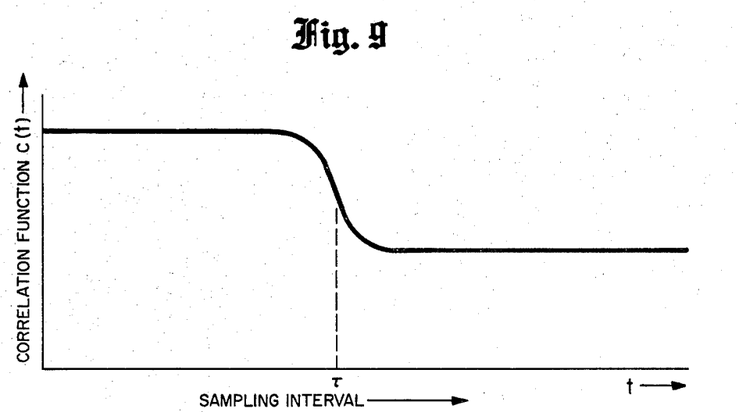
FIGS. 9 and 10 indicate schematically correlation function values as a function of the sampling intervals, for different sets of conditions.

The shape of the intensity autocorrelation function as a function of the time between samples, t, is shown schematically in FIG. 9. In general, the correlation function is large for small values of t, and then decreases to some baseline when t becomes larger than $\tau$; at times $t>>\tau$, there is no correlation between fluctuations in intensity for successive measurements since the number fluctuations will have "diffused away" between measurements. Therefore the correlation function would give just the square of the average intensity. If we assume that each particle fluoresces with intensity I, then the average intensity is $N \cdot I$ and the baseline of the correlation function is $(N \cdot I)^2$. At very short sample times, $t<<\tau$, the number fluctuations persist between intensity measurements. If we assume that the mean fluctuation in the number of particles about the average N is $\sqrt{N}$, then the autocorrelation function at short sample times, averaged over many samples, will be $I^2N^2 + I^2N$; i.e. $I^2N$ above the baseline.

Figure 10:
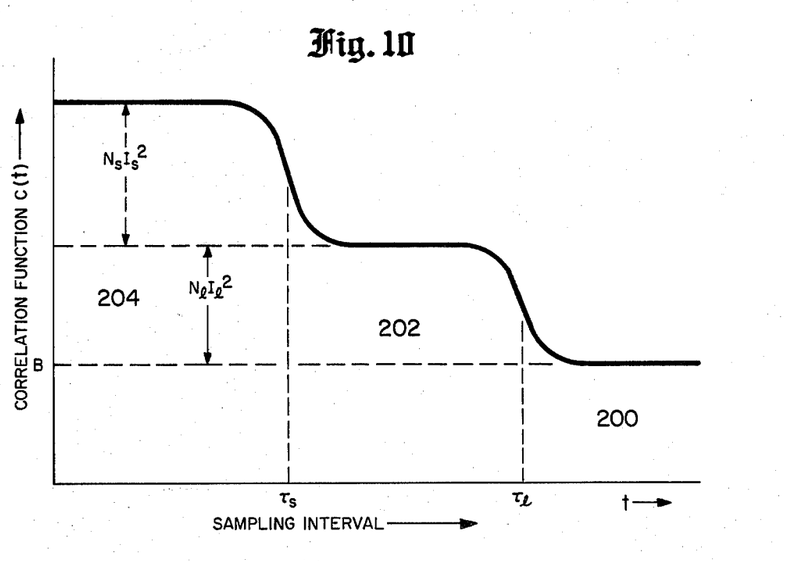

If the solution contains two species of fluorescent particles which are of different size, the correlation function would look somewhat like that shown in FIG. 10. The smaller particles have a diffusion time $\tau_s$ and the large particles have a diffusion time $\tau_l$. We assume that the averge number of large particles and small particles in the sample volume is $N_l$ and $N_s$, respectively, and that their respective fluorescent intensities per particle are $I_l$ and $I_s$. Assuming statistical independence of the two types of particles, one obtains the following values for the correlation function in three separate regions shown in FIG. 10.

| | |
|---|---|
| region 200 t >> $\tau_l$ | C(t) = B = baseline |
| region 202 $\tau_l$ > t > $\tau_s$ | C(t) = B + $N_l I_l^2$ |
| region 204 t << $\tau_s$ | C(t) = B + $N_l I_l^2$ + $N_s I_s^2$ |

One may then measure the correlation function at different sampling times and separate the fluorescence from the two different sized particles. In the immunoassay, the large particles would be the carrier particles with the fluorescence from them being due to the fluorescence from the tagged molecules bound to the carrier particles, and the small particles would be the tagged molecules not bound to the carrier particles. By measuring the autocorrelation function at different sampling times, one can separate the fluorescence from the bound molecules and the fluorescence from the free particles. If one were interested in measuring the fluorescence from the bound molecules, one would measure the correlation function in the region 202 and in the baseline region 200, and subtract the two results to obtain a measure of the amount of tagged reactant bound to the carriers. To obtain a measure of the tagged reactant which is not bound to the carrier particles (i.e. that which is "free" in solution) one would measure the correlation function in the region 204 and in the region 202, and subtract the results.

The correlation function has the property that its magnitude above baseline depends on the *square* of the intensity from each particle. Therefore bright particles contribute much more to the correlation function than dim particles. Let us say, for example, that the number of free fluorescent molecules is equal to the number of fluorescent molecules bound to the carrier particles, but that there are on the average 10 fluorescent molecules bound to each carrier particle. Under these assumptions then, there are 10 times as many free fluorescent molecules than carrier particles in a sampling volume. Although the total fluorescent light from the bound and free fluorescent molecules is the same, the bound molecules are weighted more heavily in the correlation function. For our example, $N_s = 10 N_l$, $I_l = 10 I_s$ and in region 204 of FIG. 14, the contribution to the correlation function from the bound fluorescence is 10 times the contribution from the "free" fluorescence. So, independent of the diffusion rates of the bound and free fluorescence, the correlation function emphasizes the fluorescence from the bound molecules when, on the average, more than one fluorescent molecule binds to each carrier particle.

In order to collect data at a much faster rate and increase the amount of solution which is sampled, it is advantageous to scan the solution, either by moving the incident illuminating beam, or moving the solution. One can periodically sample at hundreds or thousands of locations within the solution using in each case a sample volume of the same size, typically $\delta V \approx 10^{-6}$ cm$^3$. The correlation functions for the sample volumes are added together since the information from each sample volume is equivalent. The scanning therefore increases the rate at which one obtains the correlation function.

The baseline of the correlation function, which with one sample volume was obtained by calculating the correlation function at very long sample times (region 200 of FIG. 10), can also be computed by measuring the correlation function beteen separate volume elements, i.e.

Baseline = $<I(t) \cdot I'(t')>$ where I(t) is the intensity, at time t, from one sample volume and I'(t') is the intensity at time t' from another sample volume. It is not necessary that t' be different than t, but in a system which is scanning, only one intensity is measured at any given time. Since the fluctuations in the number of particles in different sample volumes are statistically independent, this correlation function will produce just the square of the average intensity, which is the baseline of the autocorrelation function.

As mentioned above, an experimental apparatus which was designed to make a correlation-based immunoassay measurement is shown diagrammatically in FIG. 4. The design to be described is a particular representation and is shown by way of example only. A pinhole 60, was used to define a narrow beam of (exciting) light for the purpose of illuminating a portion of the sample solution contained in sample cell 62. It was useful to employ a pinhole of diameter 100 microns (0.1 mm); other values may be chosen to be more appropriate, depending on the details of the sample solution. (discussed below). Initial experiments to assay the presence of the immunoglobulin, IgG, utilizes the antibody to IgG which was labeled with the fluorescent tag fluorescein isothiocyanate (FITC). It was convenient to employ an argon-ion laser having a collimated output beam of wavelength equal to 488 nanometers (blue). However, coherence of the exciting light source is not required for the present invention; any suitably filtered incandescent or other light source of appropriate intensity will suffice. The range of exciting wavelengths passed by the filter should ideally be substantially shorter than the useful emission wavelength range (yellow green for FITC) of the fluorescently tagged molecules.

Any sources of fluorescence in the sample solution which lie within the narrow beam volume defined by pinhole 60 in FIG. 4 will emit fluorescent light. These sources include fluorescently tagged molecules plus naturally occurring fluorescing species (e.g. contamination). The lens 64 projects this fluorescing source image onto slit 68 at the face of the photomultiplier 70. The filter 66 is used to block any 488 nanometer (blue) exciting light which may be scattered from the sample solution. The resulting light intensity which reaches the photomultiplier tube 70 will be the yellow green fluorescein emission wavelengths, together with any other long wavelengths emitted by fluorescing background impurities. It was convenient to fix the width of slit 68 at approximately 100 microns. Thus, the effective sample volume which was both illuminated and detected was on the order of $10^{-6}$ cubic centimeters, as defined by the optics employed.

The sample cell 62 is a cylindrical tube which is uniformly translated in an up/down vertical motion using a loud speaker or other suitable electromechanical transducer. Two sizes of sample tubes were used in the experiments; 6 millimeter outer diameter disposable culture tubes and two millimeter outer diameter 100 microliter micropipets. These tubes were centered within a standard one centimeter fluorimeter cuvette filled with water for the purpose of optical index matching with the incident light beam to minimize stray reflections. Sample solution volumes as small as 20 microliters are easily achieved in the small tubes.

The sample tube was translated up to 0.8 centimeter according to a triangular wave form, with the period adjustable from 0.2 to 20 seconds. The triangular driving wave form was made up of a rising and falling staircase of discrete steps, adjustable in number from 64 to 1024. Each step corresponds to a discreet sample volume. A microcomputer, such as the Motorola 6800, was employed to synchronize the sample position with the calculation of the correlation function C(t). The computer must store the measurements for one complete cycle of the scan so that it can calculate the product between the present intensity from some sample volume and the intensity obtained from that same sample volume on the previous scan, i.e.

$$I(t) \cdot I(t-\tau)$$

To obtain the baseline of the correlation function, the computer also calculates for each sample $$I(t) \cdot I'(t-t')$$

where $t' \neq \tau$. These two products are then averaged over all samples to obtain the autocorrelation function:

$$C(\tau) = <I(t) \cdot I(t-\tau)>_+$$

and its baseline value $$C'(t') = <I(t) \cdot I'(t-t')>_+$$

The scanning time was chosen to be larger than the diffusion time of the free tagged antibodies and shorter than the diffusion time of the carrier particles.

Figure 7:
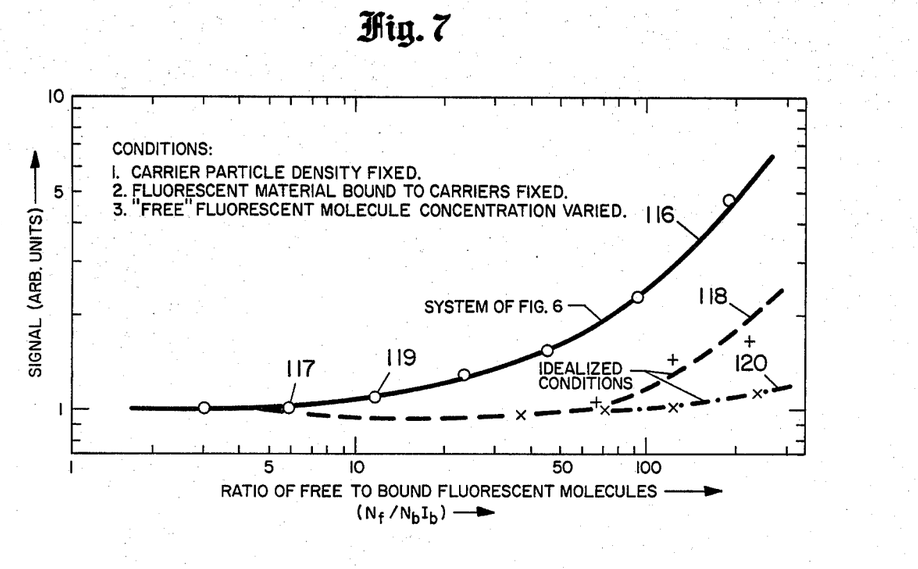
FIG. 7 shows the capability of the auto-correlation system to discriminate against the presence of a high level of radiation from free particles as compared with the radiation from the bound fluorescent material on the larger carrier particles.

The ability of the correlation assay to determine the amount of tagged IgG bound to the carrier particles in the presence of varying amounts of free fluorescently tagged antiserum or antibodies was the subject of additional tests, the results of which are shown in FIG. 7. The diffusional lifetime of the four micron diameter acrylamide beads was estimated to be roughly 6,000 seconds. The corresponding lifetime for the fluorescently tagged free molecules in solution deduced from dynamic light scattering was determined to be approximately 25 seconds. Accordingly, in order to use diffusion times to discriminate against the free tagged molecules, one should employ a scanning period $\tau$ in the order of 100 seconds.

However, we found that the fluctuation lifetime of all species, large and small, were limited to about 10 seconds by, it is assumed, velocity currents in the sample, which may be at least partially a result of the acceleration of the up/down motion of the sample cell in the configuration shown in FIG. 4 which was being employed. Accordingly, for the tests involving the system of FIGS. 6a, 6b and 6c, it was necessary to use a sufficiently low repetition rate to insure that at least the larger particles would contribute significantly to the correlated function, and a period of 1.2 seconds was selected. The plot 116 in FIG. 7 shows the correlation results, expressed in relative units, as a function of the amount of the free fluorescently tagged anti-serum or antibody, normalized to the fluorescent intensity of the bound fluorescent molecules. In the tests of FIG. 7, the IgG concentration and the carrier particle density were maintained fixed. From curve 116, we may note that when the background free fluorescence is 10 times the carrier particle fluorescence (see points 117 and 119 on curve 116), there is virtually no change in the correlation result for bound fluorescence. Thus, experimental confirmation has been obtained that the correlation assay does achieve a level of selectivity even when both fluorescing species have long enough lifetimes to contribute to the correlation. It is again noted that the rapid movement of the sample decreased the fluctuation lifetime of both types of particles and that the sample time of 1.2 seconds was not the figure which would have been preferred in the absence of the fluid current effect.

These results point out the property of the correlation technique that the correlation function goes as $I^2N$ and is therefore more sensitive to a small number of bright objects (carrier particles) than a large number of dim objects (individual free fluorescent molecules) even though the average intensity, IN, from both species is equal. So even without depending on a difference in diffusion time between the bound and free fluorescence, the technique enhances the detection of fluorescence which is bound to the carrier particles.

The plots 118 and 120 represent the results of further tests in which the fluctuation lifetime of a smaller (free) fluorescing species is diffusionally limited. In the tests which resulted in curves 118 and 120, commercially available fluorescent spheres having a diameter of 4.3 micrometers were employed for the large species and the dye rhodamine 6G was employed for the fast-diffusing species. The latter has a molecular weight of 530 with an estimated hydrodynamic radius of approximately 6.7 Angstroms. In addition, in order to reduce flow currents due to sample motion and thermal gradients, the cell sample size was drastically reduced. More specifically, a portion of a standard 100 microliter micropipet was employed, which had a 2 millimeter outside diameter, resulting in an active solution volume of less than 20 microliters. This was created in a fluorimeter cuvette filled with water for index matching, as well as temperature control. The use of the small diameter tube coincidentally reduced the volume dV by a factor of about 3 due to the focusing lens effect of the small glass tube. The resulting diffusional relaxation time out of this reduced volume for the polystyrene spheres and the rhodamine 6G were estimated to be about 3,000 seconds and 1.0 seconds, respectively. Thus, we expected that a scanning period in the order of 10 seconds should allow us to discriminate effectively against the background fluctuations of the rhodamine 6G whereas at a scanning period $\tau$ of one second, only marginal discrimination was expected.

These anticipated results are confirmed by plot 118 using a time interval $\tau$ of 1.2 seconds and plot 120 using a time interval of 10.2 seconds. It is particularly to be noted that in connection with plot 120, very little deviation in the output signal occurred even at ratios of free-to-bound fluorescent molecules well above 100. This analysis clearly demonstrates the high accuracy of this immunoassay technique when fast diffusing sources of fluorescence are employed, and where conditions are controlled so that it is practical to select a scanning period which is between the diffusion relaxation time for the larger and smaller particles.

Figure 8:
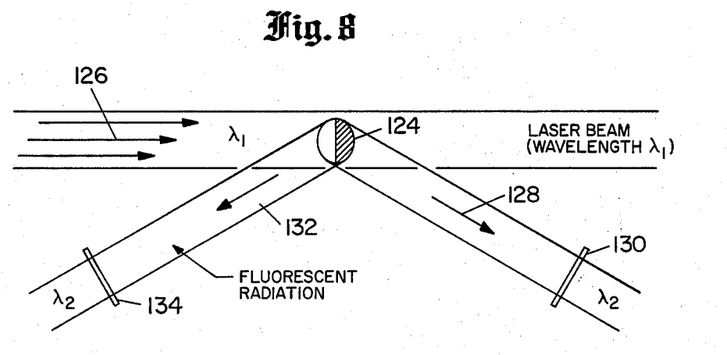
FIG. 8 is a diagrammatic showing of a shadow technique for determining the proportion of free and bound fluorescent material in the sample.

FIG. 8 of the drawings illustrates the utilization of the so-called "shadow" effect which may be used to differentiate between free fluorescent molecules as compared with bound fluorescent molecules. In FIG. 8 a large carrier particle 124 is shown being illuminated by a blue beam of collimated light 126, with fluorescent radiation being picked up in both the forward direction along path 128 through filter 130, and in the rear or back direction along path 132 through filter 134. With all of the fluorescent molecules being bound to carrier particles such as 124, and with these particles being relatively large and opaque, such as fine carbon particles, or metal coated particles, very little fluorescent illumination will be observed along path 128; but a high signal level of fluorescent radiation will be observed along path 132 as a result of the full exposure of the left-hand side of the large particle 124 to the input radiation 126. Fluorescent light from free fluorescent molecules will not be shadowed in the forward direction.

The fluorescent intensity measured along the path 128 is a measure of the number of free fluorescent molecules whereas the difference between the fluorescent intensity measured along path 132 and the fluorescent intensity measured along path 128 is a measure of the number of fluorescent molecules bound to the opaque carrier particle. If the carrier particles were semi-opaque, one may apply correction factors to the intensity measurements to obtain a measure of either the number of bound fluorescent molecules or the number of free fluorescent molecules. Mirrors and a beam chopper may also be employed to alternately measure the intensity along paths 128 and 132 with a single photodetector.

In addition, of course, the signals derived as indicated in FIG. 8 may be employed with the autocorrelation technique to provide the enhancement of detection accomplished by both of these techniques to provide an extremely sensitive immunoassay technique. Further, the system of FIG. 3 with its forward and back photomultiplier detectors and its data processor 46 including an auto-correlation capability, may be employed to implement this combined shadowing and autocorrelation system.

Background literature which is useful in the understanding and consideration of the present invention includes an article on radioimmunoassays, entitled, "A Physicist in Biomedical Investigation", by Rosalyn S. Yalow, Physics Today, October 1979, pages 25 through 29; and an article entitled "Determination of Molecular Weights by Fluctuation Spectroscopy: Application to DNA", by M. Weissman et al., Proceedings of the National Academy of Science, U.S.A., Volume 73, No. 8, pages 2776 to 2780, August 1976; and a brochure entitled, "Immuno-Fluor", dated May 1978 and published by BIO-RAD Laboratories, 2200 Wright Ave., Richmond, Calif. 94804. Incidentally, the Immuno-Fluor pamphlet describes the separation type immunoassay using fluorescent material which has been mentioned hereinabove in the present specification. Concerning the Weissman et al. article, it discloses the use of fluctuations in intensity from sampling point to sampling point to determine the number density of large fluorescent particles in solution, but there is no examination of a process or the results of a process involving the shift of fluorescently tagged molecules from solution to large carrier particles of the type described hereinabove in the present specification.

In conclusion, it is to be understood that the foregoing description and the drawings are illustrative of specific techniques of the invention. Further, the principles of the invention are clearly applicable to other immunoassay systems and to other methods of analysis wherein the reaction involves the transfer of fluorescent material between bound states on carrier particles of a large size and a "free" state where the fluorescent particles are not bound to the large carrier particles. Other electronic, optical, and mechanical techniques and systems may be employed to implement the principles of the invention. Accordingly, this invention is not limited to that precisely as shown and described hereinabove.

What is claimed is:

1. In a fluorescent, homogeneous immunoassay wherein there is provided a reagent comprising in solution carrier particles with antibodies residing at a plurality of sites on each of said carrier particles the improvement comprising:
    (a) providing said carrier particles as relatively large particles which are electromagnetically opaque both to an exciting illumination at a first frequency and to a resulting fluorescent output radiation at a second frequency;
    (b) illuminating, with optical radiation at a first frequency, the solution resulting from combining the unknown antigen with said reagent and with a fluorescently tagged immuno-active component;
    (c) optically sensing output radiation at said second frequency resulting from said fluorescent output radiation, whereby the output radiation from said sample is substantially reduced when said fluorescently tagged component becomes bound to said carrier particle;
    said sensing including the steps of (1) sensing fluorescent radiation from the "forward" direction relative to said first frequency radiation, whereby the carrier particles shield or shadow the radiation from the bound fluorescent molecules, and (2) sensing said fluorescent radiation is also in the "back" direction, to obtain full fluorescent radiation from the bound fluorescent molecules; and
    (d) comparing the signals sensed in the "forward" and in the "back" directions to determine the relative levels of bound and free fluorescent molecules, without physically separating the free and bound fluorescent components.

2. A fluorescent, homogeneous and competitive immunoassay method comprising the steps of:
    (a) providing relatively large electromagnetically opaque carrier particles in solution with antibodies residing at a plurality of sites on each of said carrier particles, said carrier particles being opaque both to an exciting illumination at a first frequency and to a fluorescent output radiation at a second frequency;
    (b) providing first and second immuno-active components; with the first being an unknown antigen to be tested, the second being tagged with a fluorescent substance;
    (c) exposing said carrier particles to the first and second components, to cause competing reactions between said first and second components with the antibodies on said carrier particles whereby the amount of fluorescently tagged component becoming bonded to said carrier particles is a function of the concentration of the unknown antigen;

(d) illuminating, with optical radiation at a first frequency, the solution resulting from combining the unknown antigen with said reagent and with a fluorescently tagged immuno-active component;

(e) optically sensing output radiation at said second frequency resulting from said fluorecent output radiation, whereby the output radiation from said sample is substantially reduced when said fluorescently tagged component becomes bound to said carrier particle;

said sensing including the steps of (1) sensing fluorescent radiation from the "forward" direction relative to said first frequency radiation, whereby the carrier particles shield or shadow the radiation from the bound fluorescent molecules, and (2) sensing said fluorescent radiation is also in the "back" direction, to obtain full fluorescent radiation from the bound fluorescent molecules; and (f) comparing the signals sensed in the "forward" and in the "back" directions to determine the relative levels of bound and free fluorescent molecules, without physically separating the free and bound fluorescent components.

3. A fluorescent, homogeneous and sandwich-type immunoassay method comprising the steps of:

(a) introducing into a sample containing as unknown antigen a reagent comprising carrier particles which are electromagnetically opaque both to an exciting illumination at a first frequency and to a fluorescent output radiation at a second frequency, said reagent containing at least sufficient binding sites to bind all unknown antigen in the sample;

(b) adding fluorescently-tagged antibody at least sufficient to bind to all the bound unknown antigen;

(c) illuminating, with optical radiation at a first frequency, the solution resulting from combining the unknown antigen with said reagent and with a fluorescently tagged immuno-active component;

(d) optically sensing output radiation at said second frequency resulting from said fluorescent output radiation, whereby the output radiation from said sample is substantially reduced when said fluorescently tagged component becomes bound to said carrier particle;

said sensing including the steps of (1) sensing fluorescent radiation from the "forward" direction relative to said first frequency radiation, whereby the carrier particles shield or shadow the radiation from the bound fluorescent molecules, and (2) sensing said fluorescent radiation is also in the "back" direction, to obtain full fluorescent radiation from the bound fluorescent molecules; and (e) comparing the signals sensed in the "forward" and in the "back" directions to determine the relative levels of bound and free fluorescent molecules, without physically separating the free and bound fluorescent components.

4. A homogeneous fluorescent analysis method as defined in claim 1, 2 or 3 including the step of selecting a series of very small volumes for sampling to include a relatively small number of said larger carrier particles in each sample so that movement of said particles into or out of the volume will cause a large fluctuation in the sensed output fluorescence.

5. An immunoassay method as defined in claim 1, 2 or 3 including the step of selecting a very small volume for sampling to include a relatively small number of the larger carrier particles so that the relative fluctuation in the number of such large particles in the volume causes a big fluctuation in output fluorescence.

6. A homogeneous immunoassay method as defined in claim 1, 2 or 3, including the step of filtering the fluorescent radiation at said second wavelength prior to optical sensing to eliminate scattered or direct radiation at said first wavelength.

* * * * *